(12) United States Patent
Kawahara

(10) Patent No.: US 8,388,934 B2
(45) Date of Patent: Mar. 5, 2013

(54) DIAGNOSTIC AGENT

(75) Inventor: Yoshirou Kawahara, Okayama (JP)

(73) Assignee: National University Corporation Okayama University, Okayama-shi (JP)

( * ) Notice: Subject to any disclaimer, the term of this patent is extended or adjusted under 35 U.S.C. 154(b) by 0 days.

(21) Appl. No.: 13/137,295

(22) Filed: Aug. 4, 2011

(65) Prior Publication Data

US 2011/0293523 A1    Dec. 1, 2011

Related U.S. Application Data

(62) Division of application No. 12/310,019, filed as application No. PCT/JP2007/065012 on Jul. 31, 2007.

(30) Foreign Application Priority Data

Aug. 8, 2006    (JP) .................................. 2006-215437

(51) Int. Cl.
    *A61K 49/00*      (2006.01)
    *A61P 1/00*       (2006.01)
(52) U.S. Cl. ........................................................ 424/9.1
(58) Field of Classification Search ........................ None
    See application file for complete search history.

(56) References Cited

U.S. PATENT DOCUMENTS

2004/0131501 A1    7/2004    Maruo et al.

FOREIGN PATENT DOCUMENTS

JP    10-194998 A    7/1998

OTHER PUBLICATIONS

Wikipedia, Colonoscopy, date accessed: Oct. 27, 2011, pp. 1-13.*
Yuki, T. et al., Evaluation of Modified Crystal Violet Chromoendoscopy Procedure using New Mucosal Pit Pattern Classification for Detection fo Barrett's Dysplastic Lesions, Digestive and Liver Disease 38 (2006), pp. 296-300.*
Yamashita, H. et al., Digestive and Liver Disease, 39, (Feb. 15, 2007) pp. 389-392.*
Pacheco, I., Dig. Dis Sci 45 (12), (Dec. 2000) pp. 2337-2346, abstract.*
Supplementary European Search Report issued in corresponding European Application No. 07 79 1696 dated Mar. 8, 2011.
Guelrud et al.: "Acetic acid improves identification of remnant islands of Barrett's epithelium after endoscopic therapy", Gastrointestinal Endoscopy, Elsevier, NL, vol. 47, No. 6, Jun. 1, 1998, pp. 512-515.
Guelrud et al.: "Enhanced magnification endoscopy: A new technique to identify specialized intestinal metaplasia in Barrett's esophagus", Gastrointestinal Endoscopy, Elsevier, NL, vol. 53, No. 6, May 1, 2001, pp. 559-565.
Form PCT/ISA/210 (International Search Report) dated Sep. 18, 2007.
Reply to Written Opinion dated Sep. 18, 2007 (with English languange translation).
Test Report to Written Opinion dated May 19, 2008 (with English language translation).
K. Togashi et al., "The Use of Acetic Acid in Magnification Chromocolonoscopy for Pit Pattern Analysis of Small Polyps", Endoscopy, 2006, vol. 38, No. 6, pp. 613-616, Georg Thieme Verlag KG Stuttgart, New York, ISSN: 0013-726X.
Kenishi Yao et al., "A Review of Current Clinical Applications of Upper Gastrointestinal Zoom Endoscopy", Digestive Endoscopy, 2005, vol. 17, No. Supplement.
Kazutomo Tagashi et al., "III Kakudai Naishikyo NI Yoru Shitsu Shindan (1) Sakusan Senshoku No Koka O Chushin Ni", Early Colorectal Cancer, 2005, vol. 9, No. 2, pp. 141-145, ISSN: 1343-2443, with English language Summary.
Tsuneo Oyama et al., "Sekkai Hakuriho (ESD) Ni Hitsuyo Na Igan Jutsuzen Shindan -Naishikyo Shindan Sokuho Shinten Shindan O Chushin Ni—Sakusan Kakudai Kansatsu O Fukumete", Stomach and Intestine, 2005, vol. 40, No. 5, pp. 761-768, ISSN: 0536-2180, with English language Summary.
Tsuneo Oyama et al., "1 ESD Shutokumae Ni Hitsuyo to Sareru Kihon Technique (1) ESD Ni Motome Rareru Jutsuzen Shindan", Rinsho Shokaki Naika, 2006, vol. 21, No. 9, pp. 1227-1233, ISSN: 0911-601X, with English language Summary.
Tsuneo Oyama et al., "[Ibyohen] ESD No Tame No Kodawari No Jutsuzen Shindan", Endoscopia Digestiva, 2006, vol. 18, No. 2, pp. 187-194, ISSN: 0915-3217 with partial English language translation.
Seastar Chemicals, Making Solutions, data acessed: Apr. 20, 2011, pp. 1-2.
Wikepedia, Acetic Acid, data acessed: Apr. 20, 2011, pp. 1-17.

* cited by examiner

*Primary Examiner* — Scott Long
*Assistant Examiner* — Lyndsey Beckhardt
(74) *Attorney, Agent, or Firm* — Buchanan Ingersoll & Rooney PC

(57) ABSTRACT

A method of conducting an endoscopic observation of an inner wall of a gastrointestine by applying a diagnostic agent to the inner wall of the gastrointestine, the diagnostic agent being an acidic aqueous solution of pH 1 to 5 containing a colorant, and conducting the endoscopic observation of the inner wall. The acidic aqueous solution can contain at least one acid selected from a carboxylic acid, hydrochloric acid, sulfuric acid and phosphoric acid. By applying the diagnostic agent to the inner wall of the gastrointestine in the endoscopic observation, it is possible to clearly observe a lesion which is difficult to be determined. In particular, the method can be used for observing lesions having cancer cells in the stomach or the Barrett's esophagus.

2 Claims, 3 Drawing Sheets
(3 of 3 Drawing Sheet(s) Filed in Color)

DIAGNOSTIC AGENT

The present application is a Divisional Application of U.S. application Ser. No. 12/310,019, filed Feb. 6, 2009, which is the National Stage of International Application No. PCT/JP2007/065012, filed Jul. 31, 2007, and claims foreign priority to Japanese Application No. 2006-215437, filed Aug. 8, 2006, the entire contents of each of which are incorporated by reference herein.

TECHNICAL FIELD

The present invention relates to a diagnostic agent to be used in endoscopic observation of the inner wall of a gastrointestine.

BACKGROUND ART

In observation of the inner wall of a gastrointestine using an endoscope, a procedure in which the observation is made easier by sprinkling a colorant has been adopted. The colorant which is widely used today is aqueous indigo carmine solution.

In operations has been used a procedure in which a resection area is clarified by marking a site to be resected with a colorant. For example, JP 10-194998 A (patent document 1) discloses a thickener and a living body marking preparation for operations which contains an intermediate color or cool color colorant applicable to the living body. This document reports that injecting the living body marking preparation to a site to be resected with a syringe allow the resection area to become clear during a surgical operation.

It, however, is not always possible to make observation easily when it is difficult to identify a lesion in the case of early cancer or the like. Moreover, it was not easy in operations to determine the margin line between a lesion and a normal mucosa or to properly resect only a lesion. Therefore, a technique by which a lesion can be observed clearly in an endoscopic observation has been awaited.
Patent document 1: JP 10-194998 A

DISCLOSURE OF THE INVENTION

Problems to be Solved by the Invention

The present invention was made in order to solve the above-described problems. The invention intends to provide a diagnostic agent which makes it possible, by being sprinkled to the inner wall of a gastrointestine in endoscopic observation, to observe clearly a lesion difficult to be determined.

Means for Solving the Problems

The above-mentioned problems are solved by providing a diagnostic agent for being sprinkled to the inner wall of a gastrointestine in endoscopic observation, comprising an acidic aqueous solution of pH 1 to 5 containing a colorant.

In this embodiment, it is preferable that the colorant is an intermediate color or cool color colorant. It is preferable that the acidic aqueous solution contain at least one acid selected from the group consisting of a carboxylic acid, hydrochloric acid, sulfuric acid and phosphoric acid. It is preferable that the acid is at least one carboxylic acid selected from the group consisting of acetic acid, malic acid and citric acid. Moreover, it is also preferable that the concentration of the carboxylic acid is 0.01 to 1 mol/L.

Effect of the Invention

The diagnostic agent of the present invention can make it possible, by being sprinkled to the inner wall of a gastrointestine at the time of endoscopic observation, to observe clearly a lesion difficult to be determined. It, therefore, can be preferably used to detection of early cancer or the like.

BRIEF DESCRIPTION OF THE DRAWINGS

The patent or application file contains at least one drawing executed in color. Copies of this patent or patent application publication with color drawings will be provided by the Office upon request and payment of the necessary fee.

BEST MODE FOR CARRYING OUT THE INVENTION

Figure 1:
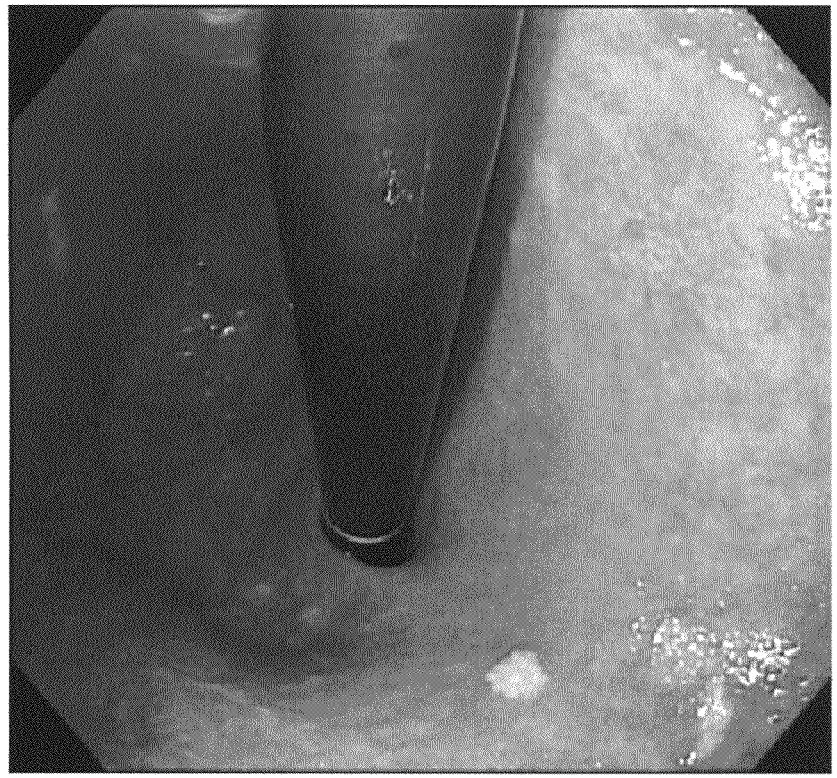
FIG. 1 is a photograph of the inner wall of the stomach observed with an endoscope in Test Example 1.

The diagnostic agent of the present invention is a diagnostic agent for being sprinkled to the inner wall of a gastrointestine in endoscopic observation, comprising an acidic aqueous solution of pH 1 to 5 containing a colorant.

The diagnostic agent of the present invention is sprinkled to the inner wall of a gastrointestine when the gastrointestine is observed with an endoscope. By being sprinkled to the inner wall of a gastrointestine, the diagnostic agent can make it easier to observe lesions on the basis of the degree of the adhesion of the agent to the surface of the inner wall of a gastrointestine. In the present invention, the method of sprinkling is not particularly restricted as long as the diagnostic agent of the present invention can be supplied to the inner wall of the gastrointestine, and it may be applying, spraying, or the like.

In the present invention, the term "gastrointestine" collectively refers to organs for digesting and absorbing foods, including liver, gallbladder and pancreas as well as gastrointestinal tract including esophagus, stomach, small intestine and large intestine or the like. Among these, the diagnostic agent of the present invention can be used suitably for stomach and Barrett's esophagus, the inner surface of which is composed of columnar epithelium. A columnar epithelium is a tissue which is particularly suitable to be applied the diagnostic agent of the present invention because it has a characteristic that its surface, which ordinarily is transparent, becomes whitish on change in pH, particularly when the acidity has become strong.

The diagnostic agent of the present invention contains a colorant. Because of this fact, the amount of the diagnostic agent having adhered to the surface to be observed is emphasized by the difference in colorant concentration, so that the margin line between a lesion and a normal mucosa can be observed clearly. Moreover, it becomes easy to observe irregularities on the surface. From the viewpoint of being distinguishable from, for example, the color of the inner wall of a gastrointestine and the color of the blood or the like, the colorant preferably is of an intermediate color or cool color, and more preferably is of a cool color. The intermediate color as referred to herein include colors other than warm colors and cool colors and examples thereof include green, purple and brown. Examples of the cool colors include blue. While the form of the colorant to be used in the present invention is not particularly restricted and it may be either a dye or a pigment, it is preferable, from the viewpoint of the easiness with which a washing operation is performed after the sprinkling, that the colorant is in the form of a dye.

The colorant to be used in the present invention is not particularly restricted, and examples thereof include Fast Green (Food Green No. 3), copper chlorophyll, sodium copper chlorophyllin, sulfobromophthalein sodium, Indocyanine Green, Methylene Blue, Brilliant Blue (Food Blue No. 1), indigo carmine (Food Blue No. 2), gardenia blue, toluidine blue, pyoktanin blue, and caramel colors. From the viewpoint of being safe to the human body without causing any adverse reaction, the colorant preferably is indigo carmine (Food Blue No. 2), gardenia blue, or a caramel color, and more preferably is indigo carmine (Food Blue No. 2) or gardenia blue, each of which is a cool color colorant.

While the concentration of the colorant to be used in the present invention may vary depending upon the type or the application site of the colorant, it is preferable, from the viewpoint that the margin line between a lesion and a normal mucosa can be observed clearly, that the colorant concentration is within the range of 0.1 to 200 mmol/L. When the concentration of the colorant is less than 0.1 mmol/L, it may become difficult to observe the difference from the color of the inner wall of a gastrointestine. It, therefore, is more preferable that the colorant concentration is 1 mmol/L or more. On the other hand, when the concentration of colorant exceeds 200 mmol/L, the color contrast decreases and, as a result, it may become difficult to observe the color contrast. It, therefore, is more preferable that the colorant concentration is 100 mmol/L or less.

The diagnostic agent of the present invention is composed of an acidic aqueous solution of pH 1 to 5 containing a colorant. Because of the fact that pH is within such a range, in many cases when the diagnostic agent of the present invention is sprinkled, secretion of mucus is promoted at a lesion, especially a lesion having cancer cells while almost no mucus is secreted at a normal mucosa. As a result, the secreted mucus makes a solution containing a colorant less prone to adhere to lesions, so that it becomes possible to clearly observe the margin line between a lesion and a normal mucosa on the basis of the difference in contrast of the colorant. Moreover, while the mucosa surface becomes whitish simultaneously because of the fact that the diagnostic agent of the present invention is an acidic aqueous solution, a lesion and a normal mucosa often become whitish to different degrees. Therefore, the margin line between a lesion and a normal mucosa is prone to become clear. Since the inner wall of a gastrointestine may be damaged when the pH is less than 1, the pH is preferably 2 or more, and is more preferably 3 or more. On the other hand, the pH is preferably 4 or less because when the pH is greater than 5, the mucus secretion at a lesion may be promoted insufficiently and, as a result, the margin line between the lesion and a normal mucosa may become unclear.

In the present invention, it is important that the solution containing a colorant is acidic. It has been known that the surface of a lesion and the surface of a normal mucosa become whitish to different degrees when an aqueous acetic acid solution is sprinkled to the inner wall of a gastrointestine. Observations, however, cannot be performed easily on the basis of only this fact. The present inventor has confirmed that a colorant is less prone to adhere either to lesions or to normal mucosa when an aqueous indigo carmine solution has been sprinkled following the sprinkle of an aqueous acetic acid solution. Therefore, it is important that the solution containing a colorant is acidic.

While the kind of the acidic aqueous solution is not particularly restricted, it is preferable that the solution contain an acid selected from among carboxylic acid, hydrochloric acid, sulfuric acid, phosphoric acid, and so on. In particular, a carboxylic acid is used preferably. While the carboxylic acid to be used is not particularly restricted, moonocarboxylic acids, such as acetic acid, propionic acid and butyric acid; oxymonocarboxylic acids, such as lactic acid, glycolic acid and gluconic acid; polycarboxylic acids, such as oxalic acid, succinic acid, glutaric acid, adipic acid, and fumaric acid; hydroxypolycarboxylic acids, such as malic acid and citric acid, and so on can be used. Among these, acetic acid, malic acid, or citric acid is more preferable from the viewpoint of safety to the human body.

While the concentration of the carboxylic acid in use in the diagnostic agent of the present invention is not particularly limited, it is more preferably 0.01 to 1 mol/L. The concentration of the carboxylic acid preferably is 0.05 mol/L or more because when the concentration of the carboxylic acid is less than 0.01 mol/L, the mucus secretion at a lesion may be promoted insufficiently and, as a result, the margin line between the lesion and a normal mucosa may become unclear. On the other hand, the concentration of the carboxylic acid is more preferably 0.5 mol/L or less because when the concentration of the carboxylic acid is greater than 1 mol/L, the inner wall of a gastrointestine may be damaged.

The use of the diagnostic agent of the present invention makes it possible to detect and observe early gastrointestinal cancers or the like, which have heretofore been difficult to be determined. The diagnostic agent of the present invention can be used suitably for early gastric cancer or early Barrett's esophagus cancer particularly among the gastrointestinal cancers.

EXAMPLES

The present invention is, illustrated below more concretely with reference to examples.

Preparation of Diagnostic Agent

A diagnostic agent of the present invention was obtained by mixing 25 ml of a 0.4 wt % aqueous indigo carmine solution (produced by Daiichi Pharmaceutical Co., Ltd.) and 15 ml of a 1.5 wt % aqueous acetic acid solution. The resulting diagnostic agent had an indigo carmine concentration of 5.3 mmol/L, an acetic acid concentration of 0.1 mol/L, and a pH of 3.0.

Test Example 1

Figure 2:
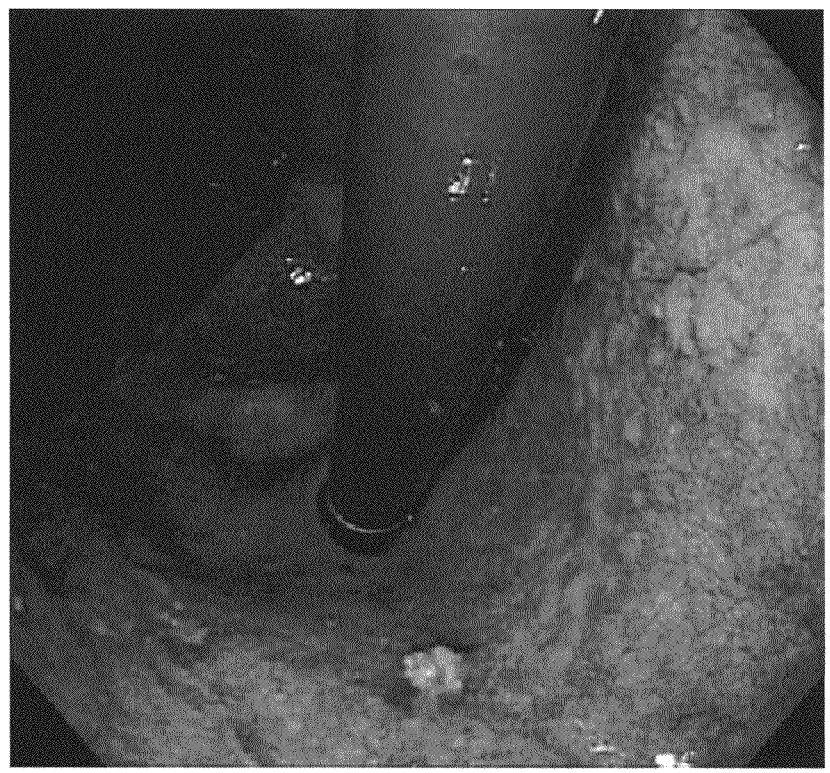
FIG. 2 is a photograph of the inner wall of the stomach observed after sprinkling only an aqueous indigo carmine solution in Test Example 1.
Figure 3:
FIG. 3 is a photograph of the inner wall of the stomach observed after sprinkling a diagnostic agent of the present invention in Test Example 1.

An upper gastrointestinal tract videoendoscope was inserted into the stomach of a 68-year-old male patient and an endoscopy was conducted. As a result, however, the presence of lesions could not be confirmed clearly as shown in FIG. 1. Only a 0.4 wt % aqueous indigo carmine solution (produced by Daiichi Pharmaceutical Co., Ltd.) was sprinkled to the inner wall of the stomach. As a result, a suspicious lesion was found as shown in FIG. 2, but no lesion could be determined clearly. The inner wall of the stomach was washed with distilled water for injection and then the diagnostic agent of the present invention prepared by the method described above. As a result, a red depressed lesion was observed clearly, as shown in FIG. 3, in a blue-stained normal mucosa as a background. The lesion was removed by endoscopic submucosal dissection, so that a well differentiated adenocarcinoma was confirmed.

Test Example 2

Figure 4:
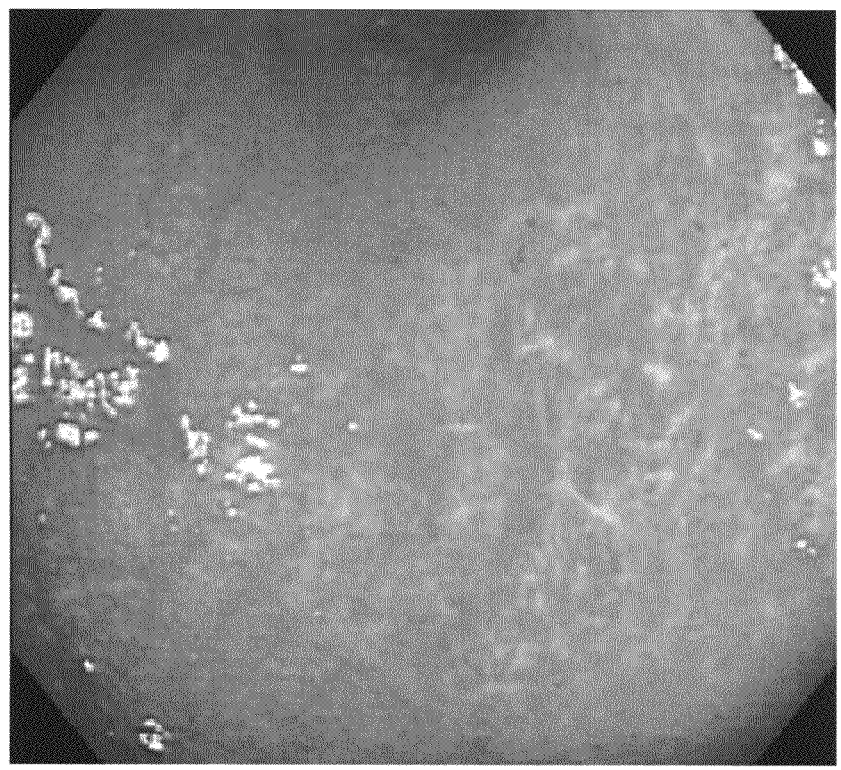
FIG. 4 is a photograph of the inner wall of the stomach observed with an endoscope in Test Example 2.
Figure 5:
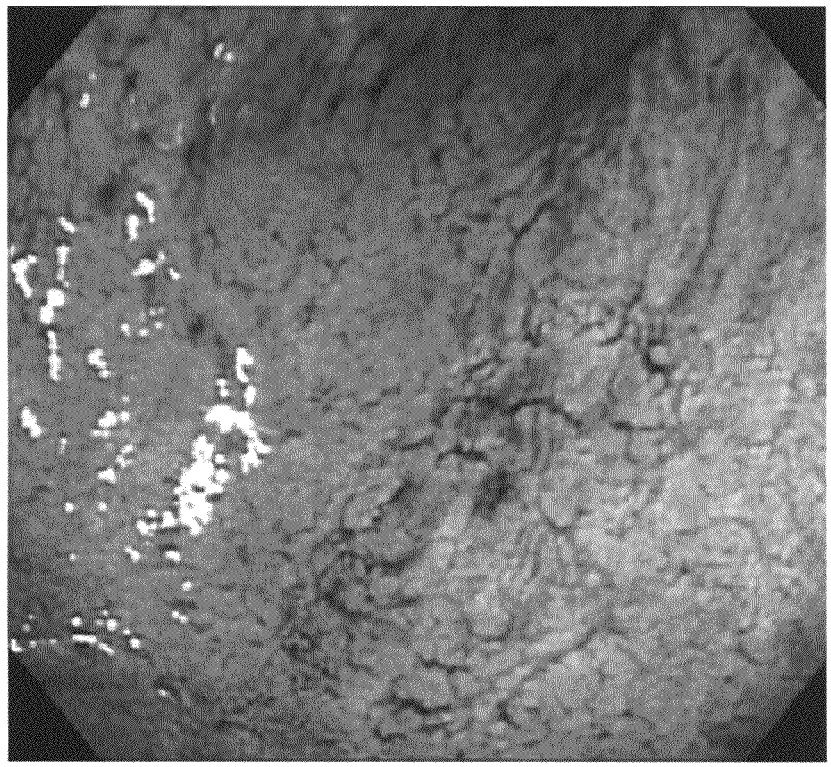
FIG. 5 is a photograph of the inner wall of the stomach observed after sprinkling only an aqueous indigo carmine solution in Test Example 2.
Figure 6:
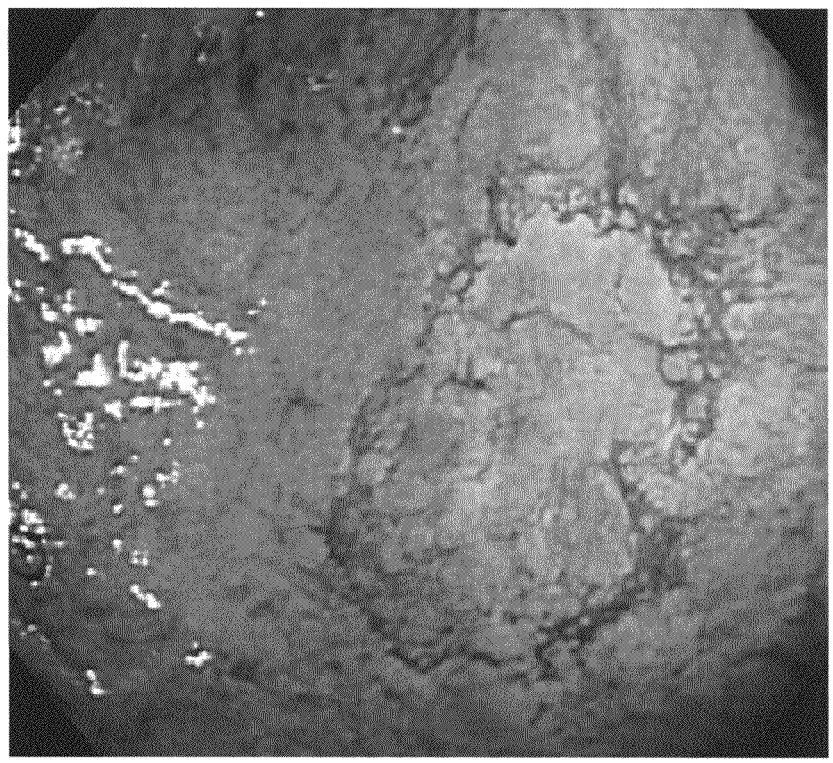
FIG. 6 is a photograph of the inner wall of the stomach observed after sprinkling a diagnostic agent of the present invention in Test Example 2.

An upper gastrointestinal tract videoendoscope was inserted into the stomach of a 29-year-old male patient and an endoscopy was conducted. As a result, however, the presence of lesions was not confirmed clearly as shown in FIG. 4. Only a 0.4 wt % aqueous indigo carmine solution (produced by Daiichi Pharmaceutical Co., Ltd.) was sprinkled to the inner wall of the stomach. As a result, a suspicious lesion was found as shown in FIG. 5, but no lesion could be determined clearly. The inner wall of the stomach was washed with distilled water for injection and then the diagnostic agent of the present invention prepared by the method described above. As a result, a lesion surrounded by a blue-stained linear depression was observed clearly as shown in FIG. 6. When this lesion was removed by surgical resection, the presence of a signet ring cell carcinoma was confirmed. The fact that it is very difficult to determine the extended area of a signet ring cell carcinoma by endoscopic diagnosis shows that the diagnostic agent of the present invention is very useful using an endoscope.

The invention claimed is:

1. A method of determining the margin line between a lesion and a normal mucosa in the inner wall of the gastrointestine comprising:
    (a) prompting secretion of mucus at a lesion by applying a diagnostic agent to the inner wall of the gastrointestine, said diagnostic agent comprising a solution containing an acetic acid and an indigo carmine, wherein said diagnostic agent has a pH of 1 to 5, and
    (b) endoscopically observing said inner wall of the gastrointestine.

2. The method according to claim 1, wherein the concentration of the acetic acid is 0.01 to 1 mol/L.

* * * * *